United States Patent [19]

Lafontaine et al.

[11] Patent Number: 5,501,228
[45] Date of Patent: Mar. 26, 1996

[54] VIBRATION SENSING GUIDE WIRE

[75] Inventors: Daniel M. Lafontaine, Plymouth; Roger Hastings, Burnsville; Daniel O. Adams, Orono, all of Minn.

[73] Assignee: SCIMED Life Systems, Inc., Maple Grove, Minn.

[21] Appl. No.: 278,552

[22] Filed: Jul. 21, 1994

Related U.S. Application Data

[63] Continuation of Ser. No. 969,743, Oct. 30, 1992.

[51] Int. Cl.⁶ ..................................................... A61B 5/00
[52] U.S. Cl. ........................................................ 128/692
[58] Field of Search ..................................... 128/673, 675, 128/687, 692, 739, 740, 772, 773, 774, 899, 902, 715, 691, 661.08, 661.07, 661.09

[56] References Cited

U.S. PATENT DOCUMENTS

| | | | |
|---|---|---|---|
| 2,949,910 | 8/1960 | Brown et al. | |
| 3,038,465 | 6/1962 | Allard et al. | 128/715 X |
| 3,930,494 | 1/1976 | Maurer et al. | |
| 3,946,724 | 3/1976 | La Balme | 128/902 X |
| 4,220,160 | 9/1980 | Kimball et al. | 128/773 X |
| 4,517,984 | 5/1985 | Perlin | 128/773 X |
| 4,733,669 | 3/1988 | Segal | 128/772 X |
| 4,815,472 | 3/1989 | Wise et al. | 128/675 |
| 4,920,967 | 5/1990 | Cottonaro et al. | |
| 4,947,852 | 8/1990 | Nassi et al. | |
| 4,986,276 | 1/1991 | Wright | |
| 5,059,851 | 10/1991 | Corl et al. | |
| 5,105,818 | 4/1992 | Christian et al. | |
| 5,174,295 | 12/1992 | Christian et al. | 128/772 X |
| 5,207,226 | 5/1993 | Bailin et al. | 128/692 X |

FOREIGN PATENT DOCUMENTS 1295727  2/1992  Canada .

*Primary Examiner*—Angela D. Sykes
*Assistant Examiner*—Samuel Gilbert
*Attorney, Agent, or Firm*—Robert E. Atkinson

[57] ABSTRACT

A percutaneous transluminal device for sensing the mechanical vibrations imparted to it inside a patient's vascular system. The preferred embodiments include a transducer attached to the distal end of a flexible guide wire. The transducer senses mechanical vibrations imparted to the guide wire in vivo and generates a corresponding electronic signal. Devices are provided for generating an audio or visual representation of the electronic signal.

19 Claims, 10 Drawing Sheets

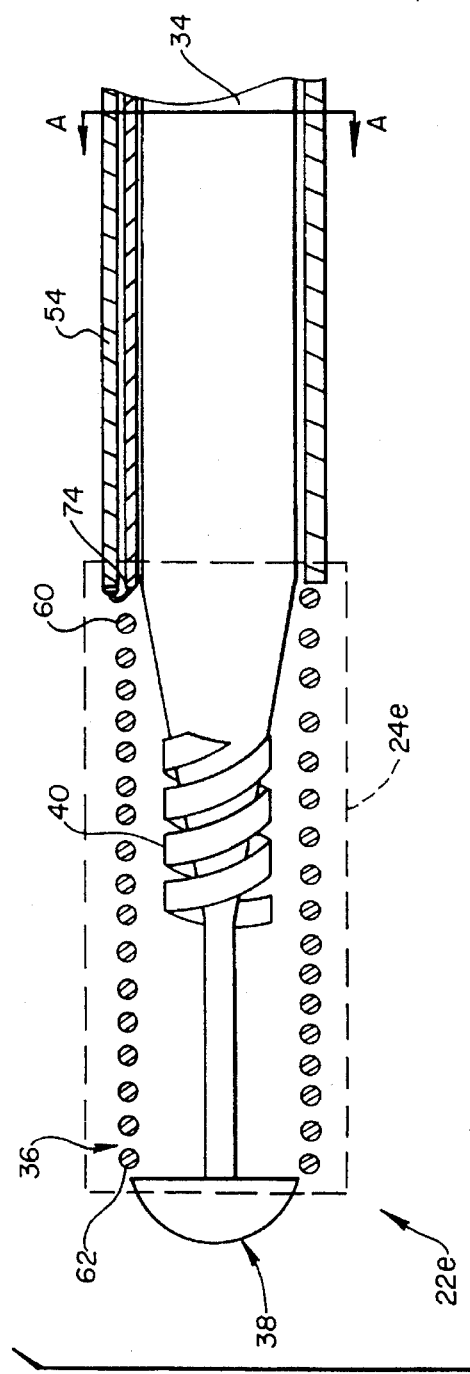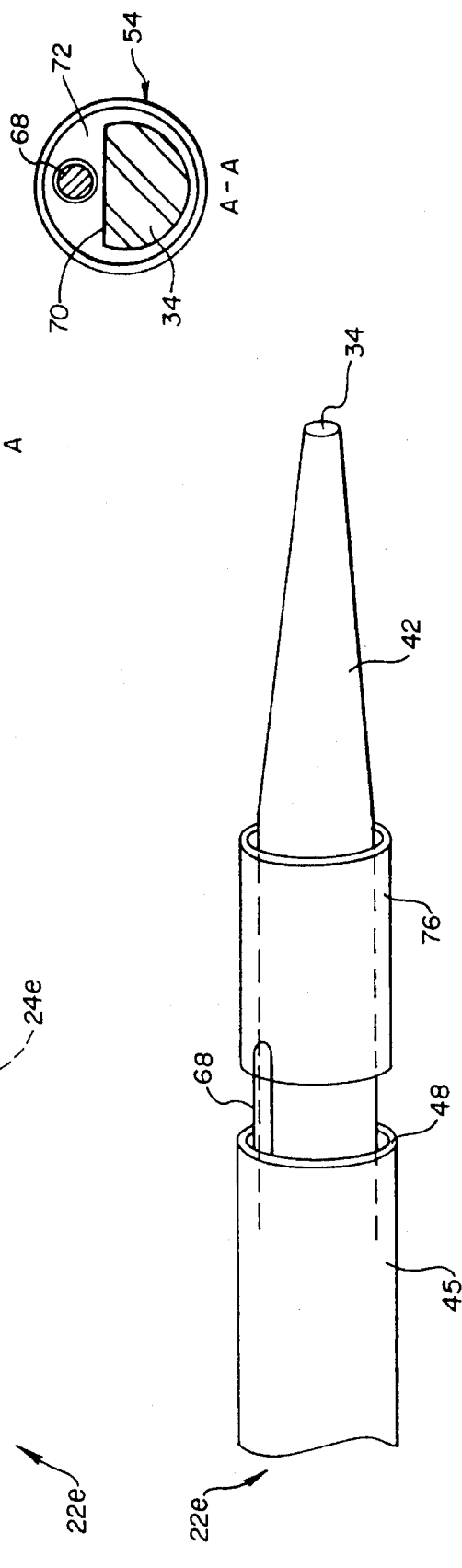

VIBRATION SENSING GUIDE WIRE

This application is a continuation, of application Ser. No. 07/969,743, filed Oct. 30, 1992.

BACKGROUND OF THE INVENTION

1. Field of the Invention

This invention relates in general to a percutaneous transluminal device for use in vascular therapy. More particularly, it relates to an improved guide wire for interactively providing information about a patient's vascular system.

2. General Description of the Art

Dilatation balloon catheters are used in a variety of blood vessel treatments such as coronary, cerebral and peripheral angioplasties. The general objective of these treatments is to open blockage caused by lesions within a vessel. For example, in percutaneous transluminal coronary angioplasty (PTCA), a guide catheter is introduced at an appropriate location in the patient's body and routed through the vascular system into the aorta and coronary orifice. A thin and relatively flexible guide wire is advanced through the guide catheter to the arteries, and then steered into side branches (if necessary) to access the lesion. Once the guide wire has established a path across the lesion, an "over-the-wire" dilatation balloon catheter is passed over the proximal end of the guide wire until the balloon is adjacent the lesion. The balloon is then inflated by introducing a fluid into the balloon through an inflation lumen in the catheter. The inflated balloon expands against the blockage to dilate the obstructed blood vessel. Another type of balloon catheter known as "fixed-wire," eliminates the need for a separate guide wire by attaching a short flexible guide wire to the distal end of the catheter.

Further details of angioplasty procedures and the devices used in such procedures can be found in U.S. Pat. Nos. 4,983,278 (Euteneuer), and 5,032,113 (Burns). The entire disclosure of each of these patents is incorporated herein by reference.

X-ray fluoroscopy is used during angioplasty to allow the surgeon to "see" the dilatation instruments on a monitor as they are maneuvered inside the body. However, catheters and guide wires are extremely thin, and therefore, they do not always generate a clearly discernable image on the monitor. Also, virtually no X-ray image is generated by lesions, arteries and other vessels in the body. Therefore, contrast media must be injected through the catheter into the vessels in order to create an image of the relevant portions of the vascular system on the monitor.

Contrast media quickly flows away with the blood flowing through the vessel, and thus the details of the vessel, including the position of any lesions, are only briefly visible. As a result, frequent injections of contrast media may be necessary, particularly if the path to the lesion is complex and difficult to negotiate. This creates a potential problem, however, since excessive amounts of contrast media may be toxic to the kidneys, liver and brain. Thus, there is a need for safer methods of obtaining information about a patient's vascular system during angioplasty.

Several patents disclose in vivo sonic devices for obtaining information about the human anatomy. A partial list of such patents includes U.S. Pat. Nos. 2,949,910 to Brown et al.; 4,986,276 to Wright; 4,920,967 to Cottonaro; and 5,059,851 to Corl. The devices disclosed in these patents essentially transmit a sonic signal in vivo and receive the reflected signal.

Other patents disclose external sonic devices for obtaining information about the human anatomy. A partial list of such patents includes U.S. Pat. No. 3,930,494 to Maurer, and Canadian patent no. 1,295,727 to Sekhar et al. These devices obtain information by transmitting and detecting sonic signals from outside the patient's body.

The present invention provides a novel approach to obtaining information about the human anatomy and physiology. The disclosed embodiments of the invention are simple and efficient guide wires that interactively provide information about a patient's vascular system during angioplasty. Such information includes the patient's general blood flow patterns and characteristics, such as stenotic flow, laminar flow, high-shear-stress flow or turbulent flow. The present invention avoids the relative complexity of sonic devices by detecting the mechanical vibrations imparted to the guide wire while it is inside the patient's vascular system.

The present invention also provides structures and methods for conducting electronic signals along a transluminal device in an simple and efficient manner. The invention further provides a simple, efficient and easy-to-use coupling mechanism for making electronic connections to the transluminal device. The coupling mechanism is also a convenient access point for gripping and steering the transluminal device.

The following terms are used throughout this disclosure and are intended to have the following meanings:

The term "distal" refers to the end of the percutaneous transluminal device that is inserted in the patient.

The term "proximal" refers to the end of the percutaneous transluminal device that remains outside the patient.

The term "impact" is used in its broadest sense to describe any type of contact, whether momentary or prolonged, and shall not be interpreted to imply the need for an extreme amount of force.

It is hereby noted that the descriptions of the art provided in this disclosure are not intended to constitute an admission that any patent, publication or other information referred to herein qualifies as "prior art" within the meaning of 35 USC § 102. Also, in accord with 37 CFR § 1.97, these descriptions shall not be construed to mean that: 1) a search has been made; 2) Applicants consider the information discussed herein to be "material" as defined in 37 CFR § 1.97; or 3) no other material information exists.

SUMMARY OF THE INVENTION

It is an object of the present invention to provide a percutaneous transluminal system for obtaining information about the human anatomy and physiology.

It is also an object of the present invention to provide an improved structure and method for conducting electronic signals along a percutaneous transluminal device.

It is also an object of the present invention to provide an improved structure and method for electronically coupling a percutaneous transluminal device to external circuitry and/or peripheral devices, while at the same time providing a convenient access point for gripping and steering the percutaneous transluminal device.

It is also an object of the present invention to provide an improved guide wire for use in angioplasty procedures.

It is another object of the present invention to provide a simple and efficient system for obtaining information about a patient's vascular system, and for converting this information into a form that may be interpreted and understood.

It is another object of the present invention to provide a simple and efficient system for obtaining information about the general blood flow patterns and characteristics of a patient's vascular system, and for converting this information into a form that may be interpreted and understood.

It is another object of the present invention to provide a simple and efficient system for obtaining information about the composition of lesions within a patient's vascular system, and for converting this information into a form that may be interpreted and understood.

These and other objects are realized in accordance with the present invention by providing a guide wire having a sensing element at its distal end for sensing mechanical vibrations imparted to the guide wire while it is inside a patient's vascular system. The mechanical vibrations may be imparted to the guide wire by contact with the patient's vessel and/or objects therein, such as flowing blood or lesions on the vessel wall. A transducer converts the mechanical vibrations to electronic signals. Conducting layers formed along the length of the guide wire transmit the electronic signals from the transducer to a coupling mechanism connected to the proximal end of the guide wire. The coupling mechanism couples the guide wire to external circuitry and peripheral devices which convert the electronic signals generated by the guide wire into an easily interpreted form, such as audible sounds or a visual display.

Thus, the invention presents several advantages. For example, it is known that the blood flow patterns in a vessel provide general information about the vessel and the heart. The inventors have discovered that a given blood flow pattern will impart a particular vibration frequency to the distal end of a guide wire. The vibration sensing system of the present invention detects different blood flow patterns by detecting the distinct mechanical vibrations imparted to the guide wire by flowing blood. The system also detects the composition of the lesions on the vessel wall by detecting distinct mechanical vibrations imparted to the guide wire through contact with the lesions. These mechanical vibrations are converted into audio or visual outputs that can be understood and interpreted by the physician.

The invention presents additional advantages by providing simple and efficient structures and methods for conducting electronic signals along a percutaneous transluminal device. In one aspect of the invention, conducting layers are formed coaxially along the length of a guide wire for conducting current. The conducting layers are conveniently constructed as part of the guide wire, and provide stable, low resistance electrical contacts, having relatively large conducting areas. In another aspect of the invention, electrical connections are made to the guide wire by filing a flat surface along the core portion of the guide wire and placing conducting leads along the flat surface. An insulating shield is placed around the core and the leads.

The invention presents even further advantages by providing a multipurpose coupling mechanism that is simple, efficient and easy to use. The coupling mechanism includes a novel sliding mechanism for securing the wire, and also includes contacts for making electrical contact with the wire's conductors. In addition, the coupling mechanism allows the physician to grip and steer the guide wire by gripping and steering the coupling mechanism.

BRIEF DESCRIPTION OF THE DRAWINGS

FIGS. 6a and 6b illustrate an alternative embodiment of the conducting mechanism shown in FIG. 1;

FIGS. 10b and 10c illustrate side and end views, respectively, of the sliding member shown in FIG. 10a;

DETAILED DESCRIPTION OF THE PREFERRED EMBODIMENTS

Figure 1:
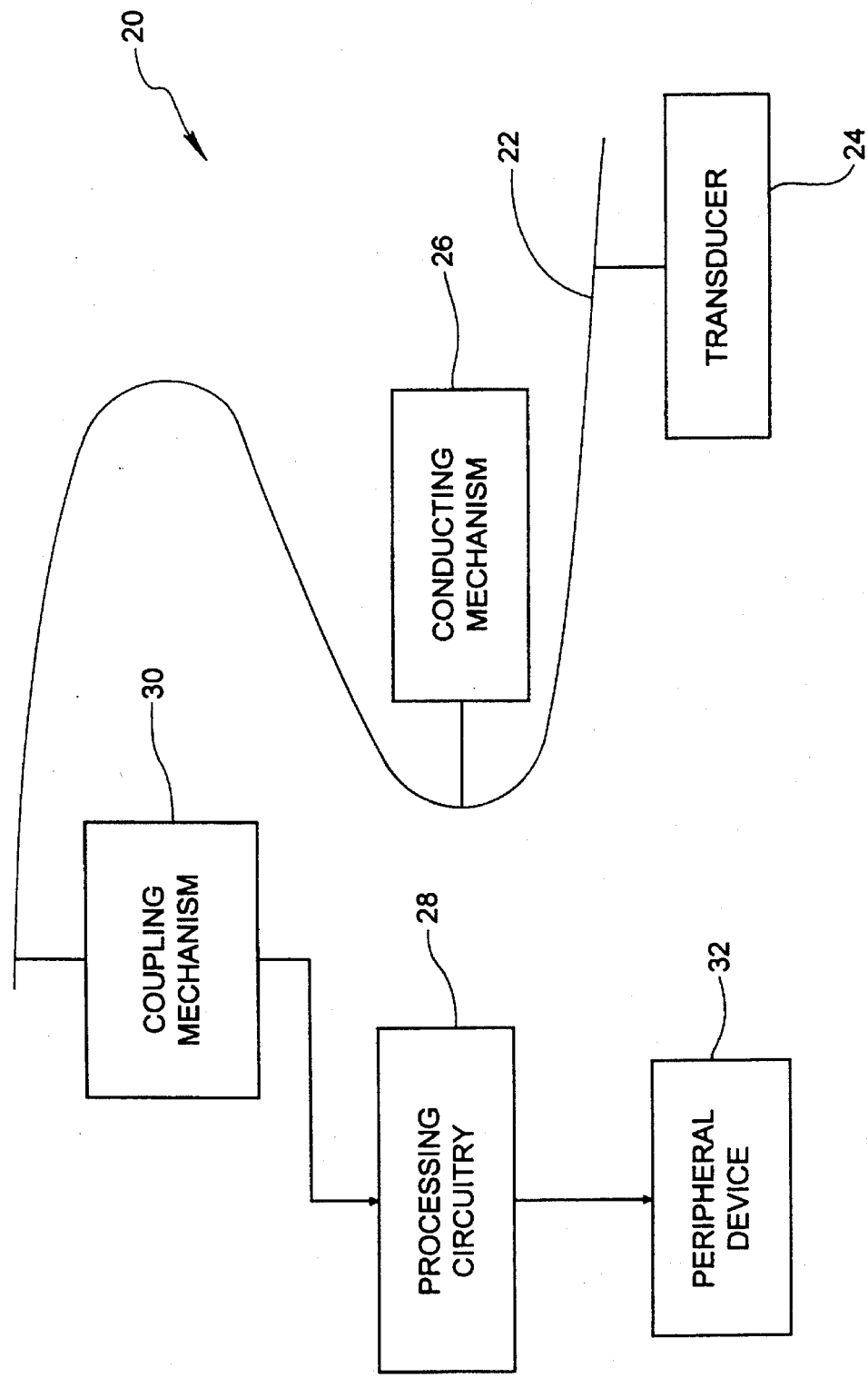
FIG. 1 illustrates a vibration sensing system embodying the features of the present invention.

FIG. 1 illustrates a vibration sensing system 20 embodying the features of the present invention. The system 20 generally includes a vibration sensing guide wire 22; a transducer 24 for converting the mechanical vibrations of the guide wire 22 into electronic signals; a conducting mechanism 26 for transmitting electronic signals along the guide wire 22; circuitry 28 for processing electronic signals from the transducer 24; a coupling mechanism 30 for transferring signals from the guide wire 22 to the signal processing circuitry 28; and a peripheral device 32 for receiving the output from the processing circuitry 28 and generating a representation of the guide wire's mechanical vibrations.

The vibration sensing system 20 may be advantageously used in connection with PTCA (percutaneous transluminal coronary angioplasty). In PTCA, a guide catheter is introduced into the patient's vascular system and advanced through the aorta to the ostium of a coronary artery. A guide wire is advanced through the guide catheter into the coronary vessels and across the lesion. A dilation balloon catheter is advanced over the guide wire and positioned adjacent to the lesion. The balloon is then inflated, thus pressing the lesion against the vessel wall to open the blockage.

The vibration sensing system 20 embodying the present invention provides a physician with information about a patient by sensing contact between the distal end of the guide wire 22 and the patient's vascular system. Such contact typically generates mechanical vibrations in the guide wire 22. These vibrations are converted into audio and/or visual representations that can be understood and interpreted by the physician.

The present inventors have discovered that certain vascular conditions impart a distinct vibration frequency to a guide wire. For example, a guide wire moving through a relatively patent vessel experiences different mechanical vibrations than a guide wire negotiating its way across a lesion. Similarly, a guide wire exposed to a turbulent blood flow pattern experiences different mechanical vibrations than a guide wire exposed to a laminar blood flow pattern. The system 20 senses these distinct vibrations and converts them into electronic signals which are fed via the conducting mechanism 26 and the coupling mechanism 30 to the processing circuitry 28 and the peripheral device 32.

The peripheral device 32 may be a conventional loudspeaker. Thus, as the physician advances the vibration sensing guide wire 22 through the patient, distinct sounds are generated at the loudspeaker whenever the distal end of the guide wire 22 contacts another object such as the guide catheter (not shown), a vessel wall (not shown), a lesion (not shown), or blood flowing in the patient's vessel. If the distal end of the guide wire 22 is exposed to a turbulent blood flow pattern, the loudspeaker output may be a swishing sound. If the guide wire 22 impacts a hard calcified lesion, the loudspeaker output may change to a sharp scraping sound. If the lesion is relatively soft, the loudspeaker output may be a subdued sound that is less harsh than the scraping sound associated with a hard calcified lesion.

The peripheral device 32 may be a visual device that is capable of representing the guide wire vibrations graphically, such as a monitor, an oscilloscope, a fast fourier transformer (FFT), a frequency spectrum analyzer, a chart recorder, or a computer. Thus, the same distinctions that are "heard" from the loudspeaker may be "seen" on the visual device. The visual device is particularly useful when the guide wire vibrations occur in the extremely low frequency range from about 1 to about 20 hz. These frequencies are too low to generate an audible sound, but they are easily represented on a visual device.

The peripheral device 32 may also be provided with sufficient discriminating electronics and/or software to automatically associate a particular output from the guide wire 22 with a particular condition. For example, if the peripheral device 32 is a computer, it may be programmed to recognize that a signal with certain characteristics indicates that the guide wire 22 is probably being exposed to turbulent flow. The physician could be alerted to this condition by a graphic, video or text prompt on the computer screen.

Figure 2:
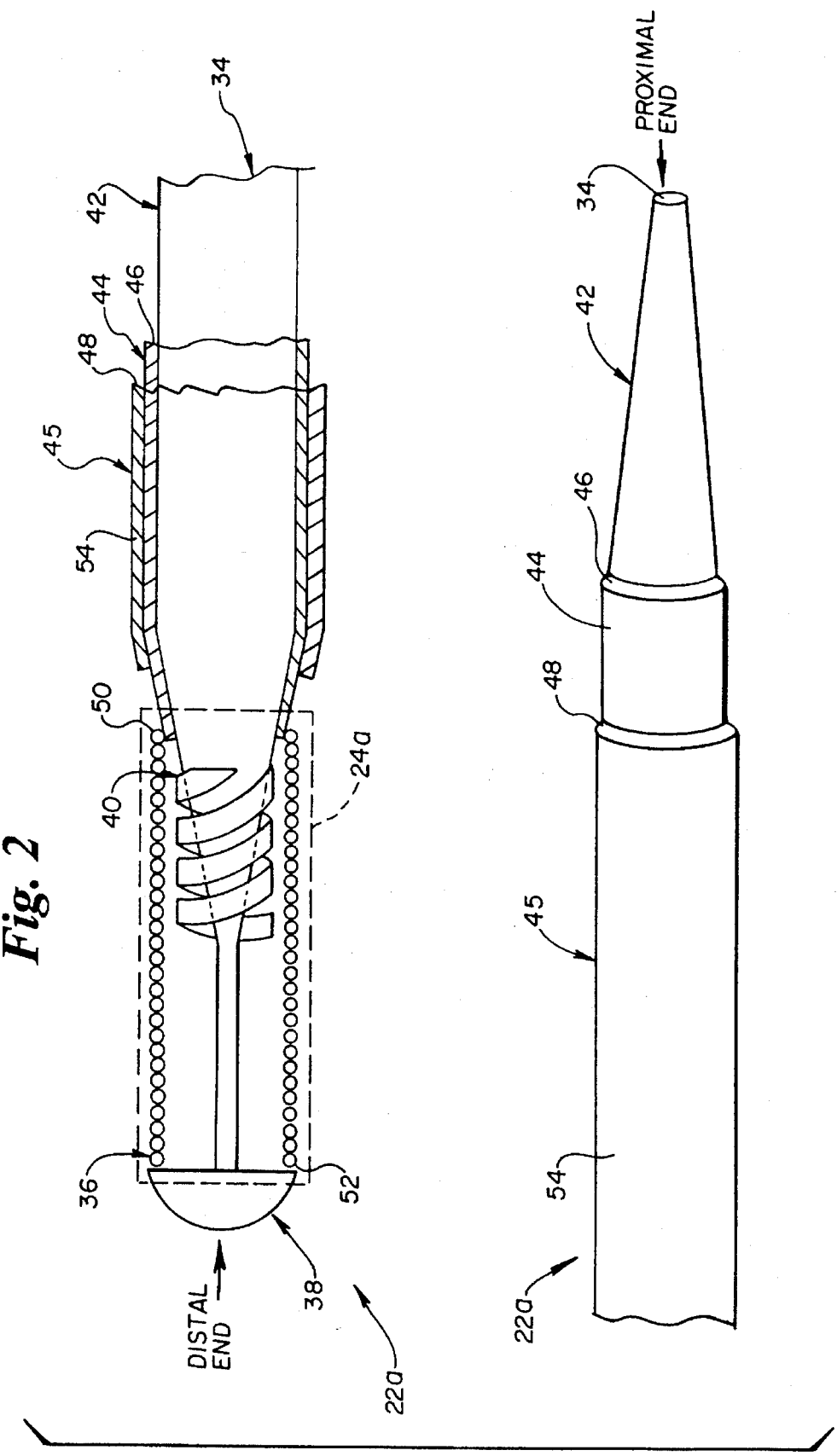
FIG. 2 illustrates one embodiment of the guide wire and transducer element shown in FIG. 1.

FIG. 2 illustrates at 22a one embodiment of the guide wire 22 shown in FIG. 1. The basic configuration of the guide wire 22a includes a conventional tapered inner core 34 extending approximately the entire length of the guide wire 22a. The core 34 is made from stainless steel which provides the desired combination of steerability, torqueability and trackability. For coronary applications, the core 34 may be approximately 0.01 inch in diameter at its proximal end, and approximately 0.003 inch in diameter at its tapered distal end. For other applications, such as peripheral, the conventional guidewire is larger than for coronary applications. The entire guide wire 22a is approximately 67 inches long. Spring coils 36 at the distal end of the guide wire 22a provide additional flexibility. The spring coils 36 are wound to a 0.018 inch outer diameter (OD) from a 0.002 inch insulated platinum wire. The length of the coils 36 is approximately 1.5 inches. The spring coils 36 and the tapered distal end of core 34 are welded directly to a weld ball 38 at the distal tip of the guide wire 22a. Alternatively, the guide wire 22a may include a forming ribbon (not shown) between the distal tapered end of the core 34 and the weld ball 38. A forming ribbon is a thin flat piece of stainless steel which is easily bent in order to shape the distal end of the guide wire 22a.

FIG. 2 illustrates at 24a one embodiment of the transducer 24 shown in FIG. 1. The transducer 24a includes a magnet 40 and spring coils 36. The magnet 40 is a thin strip of magnetic material, such as arnechrome, which is spiral wound around the distal end of the guide wire 22a. The spiral windings allow the spring coil 36 to be interweaved in the space between the magnetic strips. The magnet 40 is wound tightly to secure it around the distal end of the guide wire 22a. Alternatively, the magnet 40 may be secured by a suitable adhesive or any other suitable means. The magnetic strip 40 measures approximately 0.03 inch in width, 0.23 inch in length, and 0.003 inch in thickness.

The spring coils 36 also function as sensing coils by vibrating whenever the distal end of the guide wire 22a vibrates. The spring/sensing coils 36 are close enough to the magnet 40 to be within its magnetic field, and thus, when the coils 36 vibrate, electromagnetic signals are generated in the coils 36.

The inner core 34 is coated with layers of conducting material 42, 44 (conducting mechanism 26 shown in FIG. 1) which provide a path for current to travel along the guide wire 22a. Insulating layers 46, 48 separate and insulate the conducting layers 42, 44. The electronic signals from the spring/sensing coils 36 are transmitted along the conducting layers 42, 44 which are staggered at the distal end of the guide wire 22a to facilitate contact with the spring/sensing coils 36. The proximal end 50 of the spring/sensing coils 36 makes electrical contact with the second conducting layer 44 via a spot weld, and the distal end 52 of the spring/sensing coils 36 makes electrical contact with the first conducting layer 42 via the weld ball 38. Alternatively, electrical contact between the spring/sensing coils 36 and the conducting layers 42, 44 could be established by leads (not shown). A gold-plated polyimide shield 54 encases the second conducting layer 44 to insulate and shield the conducting layers 42, 44. The polyimide portion of the shield 54 acts as a second insulating layer 48. The gold portion of the shield acts as a third conducting layer 45 which minimizes noise. The shield's exterior surface may be coated with a low friction material such as Teflon™ (available from DuPont, located in New Cumberland, Pa.) or any medical-grade silicone coating. A slide grip coupling mechanism (shown at 30a in FIG. 7) is connected to the conducting layers 42, 44, 45 at the proximal end of the guide wire 22a for removing the electronic signals from the guide wire 22a and transferring them to the processing circuitry 28. The details of the slide grip coupler 30a are provided later in this disclosure.

Figure 3:
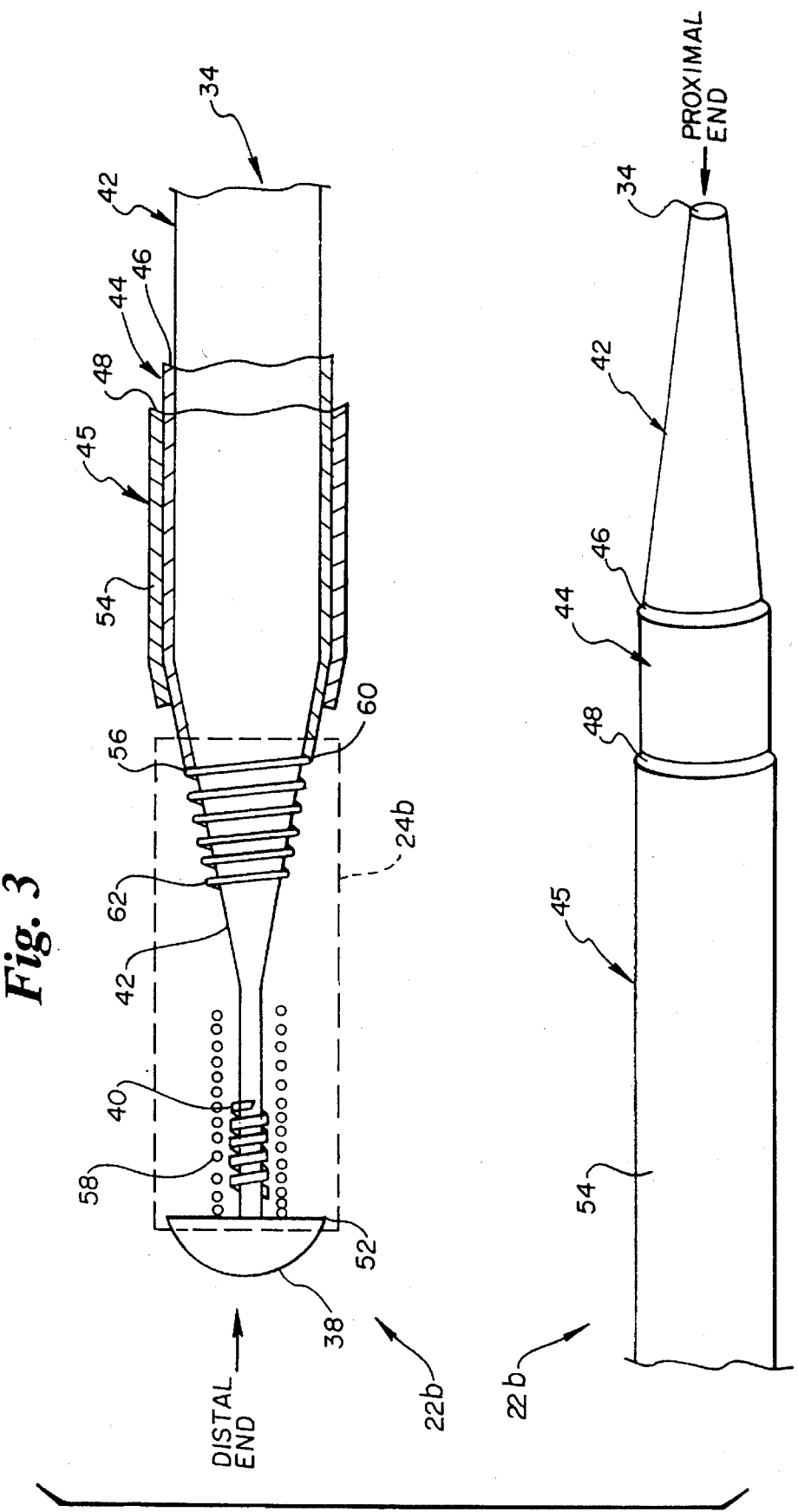
FIG. 3 illustrates a second embodiment of the guide wire and transducer element shown in FIG. 1.

FIG. 3 illustrates at 22b and 24b another embodiment of the guide wire 22 and transducer 24 shown in FIG. 1. The transducer 24b includes a magnet 40 and a set of sensing coils 56 which, unlike the previous embodiment, are separate from the spring coils 58. The magnet 40 is a thin strip of magnetic material, such as arnechrome, which is wound securely around distal end of the guide wire 22b. Alternatively, the magnet 40 may be secured by an adhesive or any other suitable means. The sensing coils 56 are made from insulated platinum, and may be secured to the guide wire 22b by an adhesive or any other suitable means.

The magnet 40 shown in FIG. 3 vibrates whenever the flexible distal tip of the guide wire 22b vibrates, and the sensing coils 56 are positioned close enough to the magnet 40 to be within its magnetic field. Thus, the relative movement of the sensing coils 56 within the magnetic field generates electromagnetic signals in the sensing coils 56 which are transmitted to the conducting layers 42, 44.

The conducting layers 42, 44 shown in FIG. 3 are staggered at the distal end of the guide wire 22b to facilitate contact with the sensing coils 56. The sensing coils 56 are attached to the distal end of the guide wire 22b such that the proximal end 60 of the sensing coils 56 contacts the second conducting layer 44, and the distal end 62 of the sensing coils 56 contacts the first conducting layer 42. Alternatively, leads (not shown) could be used to establish contact between the sensing coils 56 and the conducting layers 42, 44.

Figure 4:
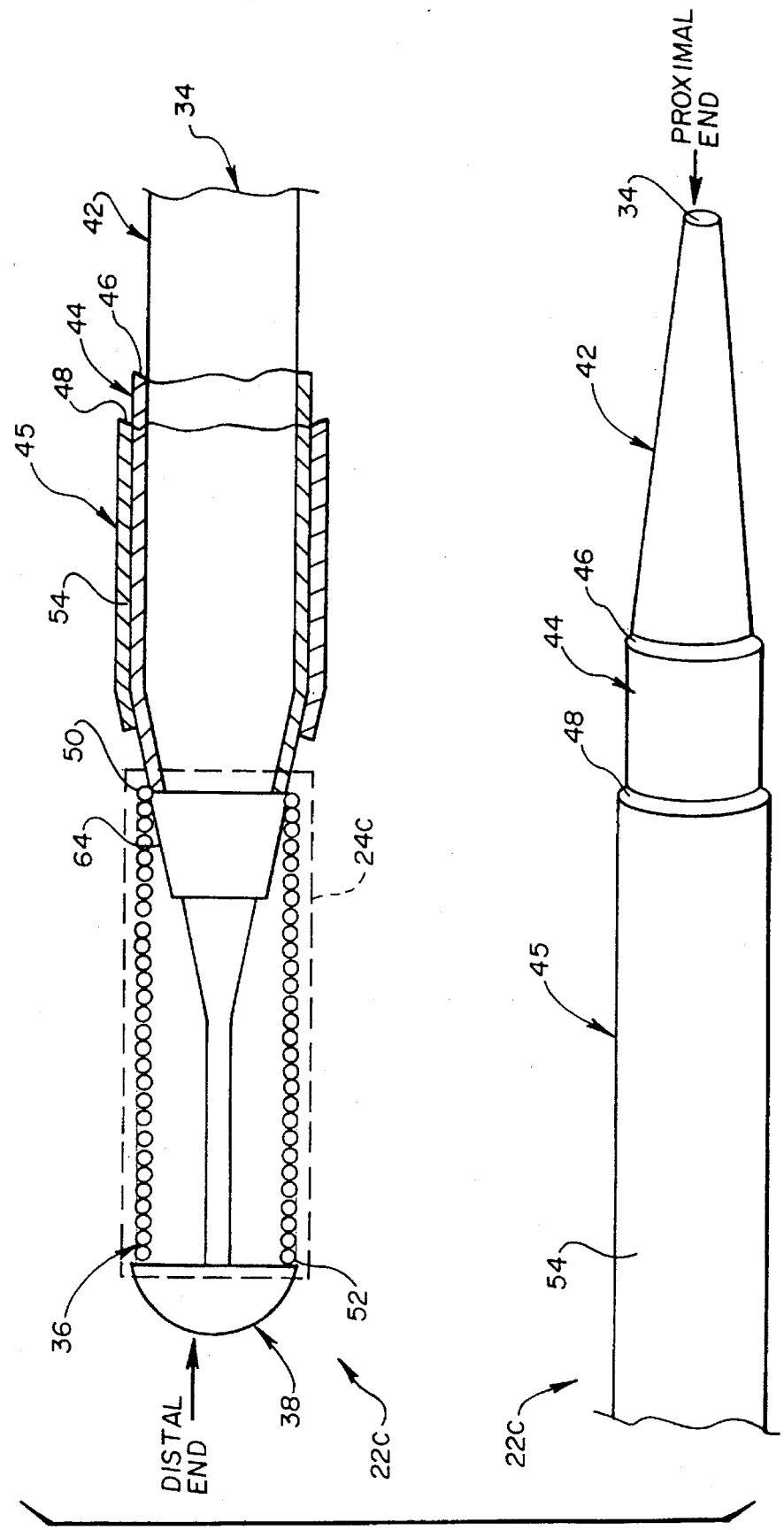
FIG. 4 illustrates a third embodiment of the guide wire and transducer element shown in FIG. 1.

FIG. 4 illustrates at 22c and 24c yet another embodiment of the guide wire 22 and transducer 24 shown in FIG. 1. The transducer 24c includes a piezoelectric crystal 64 and spring/sensing coils 36. The crystal 64 and the spring/sensing coils 36 are mechanically coupled together in any suitable manner so that vibrations experienced by the spring/sensing coils 36 are transferred directly to the crystal 64 which is electronically connected to the conducting layers 42, 44. Thus, as the flexible distal portion of the guide wire 22c vibrates, the spring/sensing coils 36 and the crystal 64 also vibrate. The crystal 64 generates an electronic signal corresponding to the detected vibrations, and this signal is transferred to the conducting layers 42, 44.

It is contemplated that other transducer configurations would also be suitable for the disclosed invention. For example, a fiber optic transducer could be implemented by applying a reflective material to the interior of the spring/sensing coils 36 and transmitting light through a beam splitter, along a fiber to the interior of the spring/sensing coils 36. As the coils 36 vibrate, the intensity of the light reflected from the coils 36 would vary accordingly, thereby generating a reflected light signal corresponding to the vibrations at the distal end of the guide wire 22. The reflected light signals could be transmitted through the same fiber to the beam splitter which separates the reflected light from the source light, and directs it to a detector.

Figure 5:
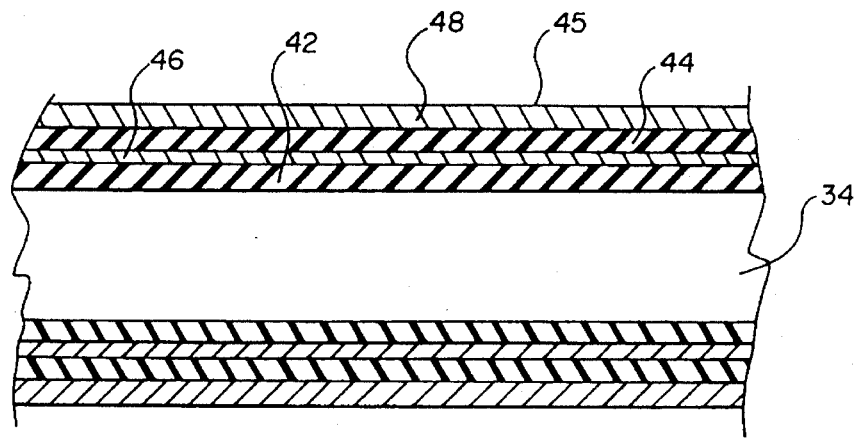
FIG. 5 illustrates one embodiment of the conducting mechanism shown in FIG. 1.

FIG. 5 is a cross-section view of a central portion of the guide wire 22 further illustrating the conducting layers 42, 44, 45 and the insulating layers 46, 48. The layers may be applied by a number of conventional methods such as metal plating, deposition, or sputter coating. Because the guide wire 22 is tapered, extra care must be taken during the manufacturing process to ensure a uniform thickness of the applied layers. The first conducting layer 42 is preferably gold and is applied directly to the core wire 34. Gold provides several desirable properties, including biocompatability and low resistance. The first insulating layer 46 is preferably Kapton™ (available from DuPont located in New Cumberland, Pa.) or polyimide, and it is applied directly to the first conducting layer 42. The second conducting layer 44 is also gold and is applied directly to the first insulating layer 46. The shield 54 covers the second conducting layer 44. The shield 54 is made from polyimide and also serves as the second insulating layer 48. A third gold conducting layer 45 is applied to the shield 54 to minimize noise.

The use of conducting layers to transmit electronic signals along the guide wire 22 provides several advantages. The conducting layers 42, 44, 45 are conveniently constructed as part of the guide wire 22, and thus the need for attaching external conductors is eliminated. Because the conducting layers 42, 44, 45 extend around the circumference of the core wire 34, they provide a relatively large contact area and conducting area. Thus, they also provide low resistance and better overall conductance. The negative results associated with moving cables and triboelectric effects are reduced since there is no relative movement between the conductors. The coaxial design of the conducting layers allows the third conducting layer 45 to insulate the first and second conducting 42, 44 from noise generated by external E-fields.

FIGS. 6a and 6b illustrate at 22e still another embodiment of the guide wire 22 and conducting mechanism 26 shown in FIG. 1. The general construction of the transducer 24e shown in FIG. 6a is the same as the embodiment 24a shown in FIG. 2. The transducer 24e includes a magnet 40 and spring coils 36 which also serve as sensing coils. The magnet 40 is a thin strip of magnetic material, such as arnechrome, which is spiral wound securely around distal end of the guide wire 22e. The spring/sensing coils 36 are insulated platinum conductors that experience mechanical vibrations when the distal end of the guide wire 22e experiences mechanical vibrations. The spring/sensing coils 36 are close enough to the magnet 40 to be within its magnetic field, and thus, the mechanical vibrations of coils 36 generate electromagnetic signals in the coils 36.

The guide wire 22e shown in FIGS. 6a and 6b includes three conductors. One conductor is a layer of gold 42 formed on the core wire 34. The second conductor is an insulated silver wire 68 which extends along the length of the guide wire 22e and is encased by a polyimide tube 54. The third conductor is a layer of conducting material 45 formed on the polyimide tube 54 which coaxially surrounds the core wire 34 and first conducting layer 42. As seen in FIG. 6b, the silver wire 68 is accommodated against a flat portion 70 formed along the length of the core wire 34. The space between the polyimide tube 54 and the flat portion 70 forms a lumen 72 through which the silver wire 68 extends. Conductors 42 and 68 are connected to the spring/sensing coils 36 at the distal end of the guide wire 22e. The first conducting layer 42 is connected to the distal end 62 of the spring/sensing coils 36 via the weld ball 38. The silver wire conductor 68 is connected to the proximal end 60 of the spring/sensing coils 36 via a welded connection 74.

The conductors 42, 68 and 45 are staggered at the proximal end of the guide wire 22e to facilitate connection to a coupling mechanism 30, 30a (shown in FIGS. 1 and 7–10c). The proximal end of the silver wire conductor 68 is coupled to a conducting band 76 which is substantially coaxial with the inner core wire 34. The first conductor 42 extends further in the proximal direction than the conducting band 76, and the conducting band 76 extends further in the proximal direction than the third conductor 45.

FIGS. 7–10c illustrate at 30a the details of a preferred embodiment of the coupling mechanism 30 shown in FIG. 1. Coupling mechanism 30a is referred to herein as a "slide grip" electrical coupler and provides a convenient, efficient and easy-to-use structure for making electrical contact with the conducting mechanism 26 at the proximal end of the guide wire 22. The coupler 30a is based on the gripping device disclosed in U.S. Pat. No. 5,137,517 which is assigned to the assignee of the present invention. The entire disclosure of U.S. Pat. No. 5,137,517 is incorporated herein by reference.

It is often necessary for the physician to twist or rotate the guide wire 22 in order to steer it through the patient's vascular system. This is particularly true for the disclosed vibration sensing system 20 since information is derived from the guide wire's contact with various objects, and thus the physician may need to maneuver the guide wire 22 in order to initiate these contacts. Because a typical guide wire is formed from a small diameter wire, it is difficult for the physician to grasp it securely, and accordingly, it is difficult to control the amount of rotation. The slide grip coupler 30a allows the physician to twist, rotate, or otherwise contort the guide wire 22 by gripping and maneuvering the coupler 30a.

The slide grip coupler 30a generally comprises a substantially cylindrical body member 78 with a longitudinal slot 80 for laterally receiving the proximal end of the guide wire 22.

A sliding member 82 is also received within slot 80 and is movable longitudinally relative to body member 78 to bring together a pair of opposed surfaces on body member 78 and sliding member 82 to hold the guide wire 22 tightly therebetween. Once the guide wire 22 is so engaged, rotation of the coupling mechanism 30*a* rotates the guide wire 22 in a 1:1 relationship, which is important when steering the guide wire 22 through the patient's vascular system by twisting the proximal portion thereof to direct the distal portion of the guide wire 22.

The body member 78 has a substantially cylindrical main portion 84 with a frusto-conical portion 86 at its distal end. At its proximal end, the body member 78 has a laterally flat end wall 87 with an opening therethrough and into slot 80 for longitudinally receiving sliding member 82. The outer surface the cylindrical main portion 84 is defined by a plurality of longitudinal ribs 88 which facilitate manipulation of the coupler 30*a* and provide tactile feedback to the physician for determining the degree of rotation.

Figure 7:
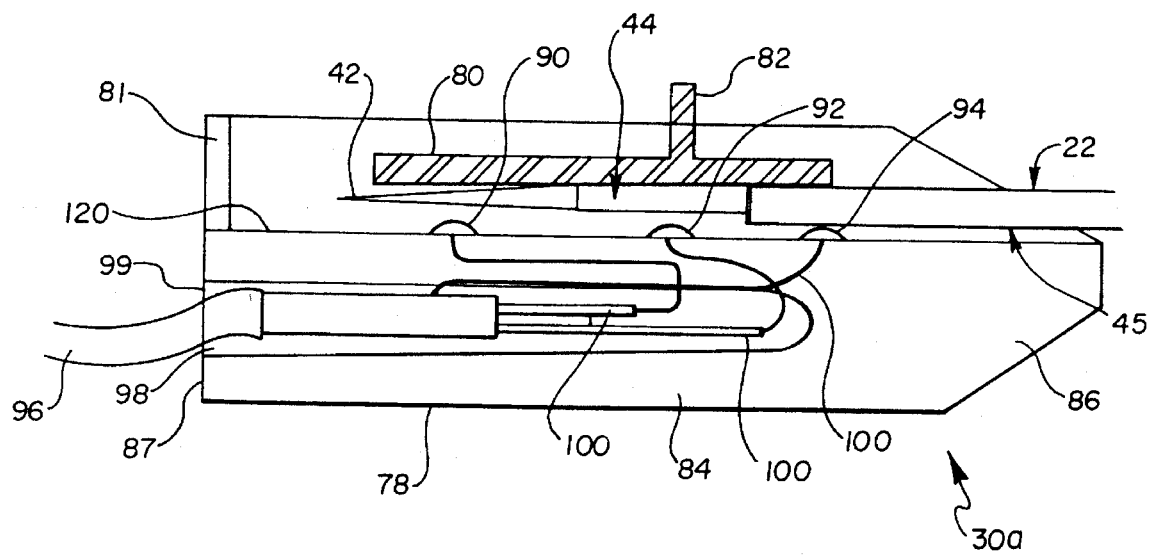
FIG. 7 illustrates one embodiment of the coupling mechanism shown in FIG. 1.
Figure 8A:
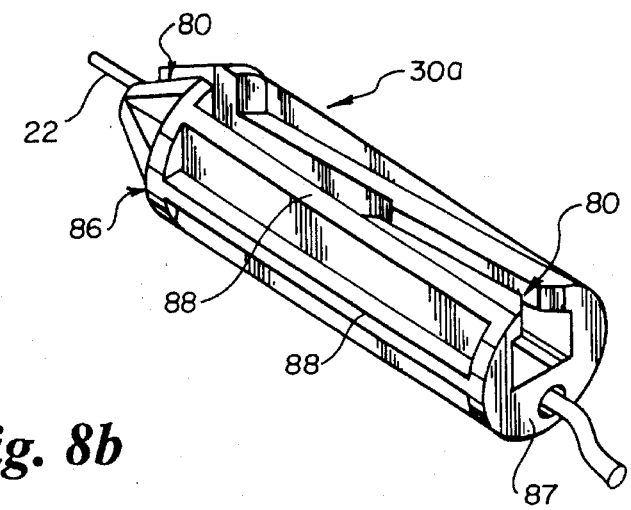
FIGS. 8a, 8b and 8c illustrate the lateral insertion of a guide wire into the coupling mechanism shown in FIG. 7.
Figure 8B:
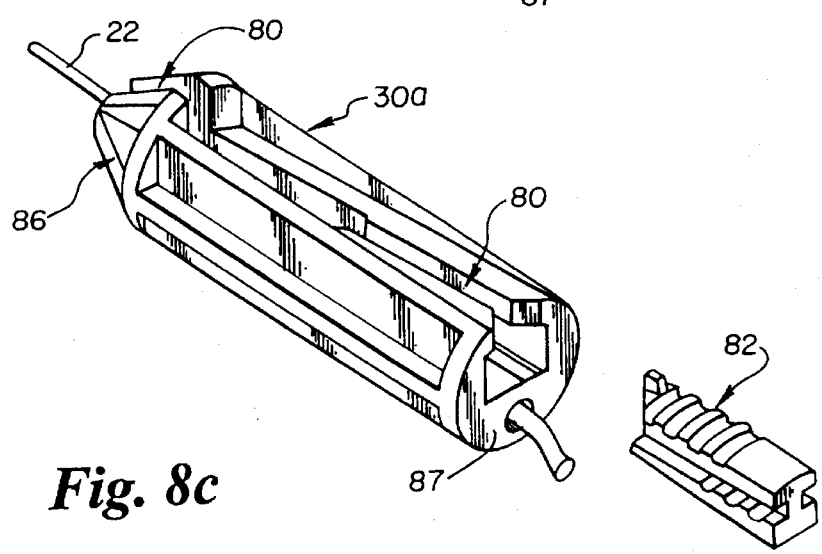
Figure 8C:
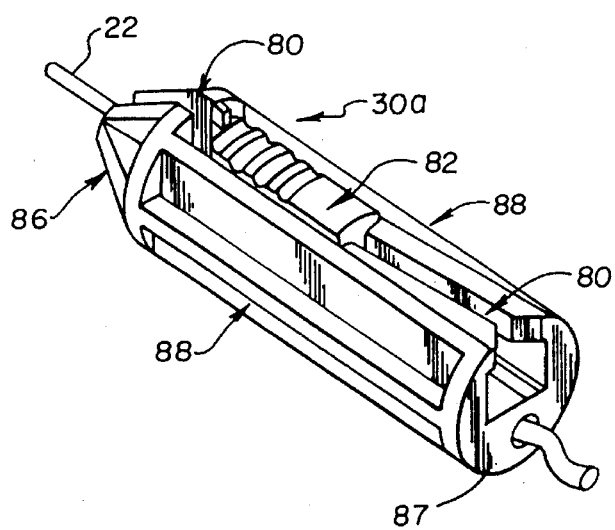

As shown in FIG. 7, the slot 80 includes a series of spaced-apart spring loaded contacts 90, 92, 94 which extend through bottom surface 120. The guide wire 22 shown in FIGS. 7 and 8*a*–8*c* include conducting layers 42, 44, 45, which are staggered at the proximal end of the guide wire 22 to facilitate making electrical contact with the spring loaded contacts 90, 92, 94. The conducting mechanism (42, 44, 68, 76) shown in FIGS. 6*a* and 6*b* is also staggered at the proximal end of the guide wire 22*e* to facilitate making electrical contact with the spring loaded contacts 90, 92, 94. Optionally, an alignment wall 81 may be placed at the proximal end of the slot 80 to ensure proper positioning of the conductors (42, 44, 45, 76) over the contacts 90, 92, 94. An electrical cable 96 extends through a cavity 98 and an opening 99 in the body member 78. One end of the cable 96 is electrically coupled to the spring loaded contacts 90, 92, 94 via leads 100. The opposite end of the cable 96 is coupled to the processing circuitry 28, 28*a*, 28*b* (shown in FIGS. 1, 11 and 12).

The sliding member 82 has an overall shape similar to an I-beam (see FIG. 10*c*), with an upper cross member 102, lower cross member 104 and central upright longitudinal beam 106. An upper, laterally arcuate surface 108 of upper member 102 has a series of lateral grooves 109, 110, 111 and 112 thereon, which provide an enhanced grip for the thumb or finger of the physician. In addition, knob 114 on upper surface 108 (see FIG. 10*b*) provides a tactile feel indicator on sliding member 82, to permit the physician to determine the orientation of coupler 30*a*, or to count the number of rotations thereof in use. A bottom surface 116 of lower member 104 is centrally flat, with rounded proximal and distal end corners 117, 118.

Figure 9A:
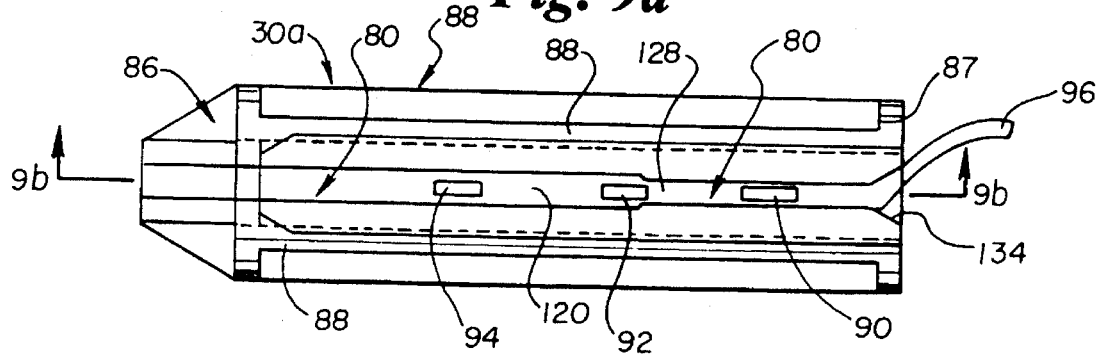
FIGS. 9a and 9b illustrate the body member portion of the coupling mechanism shown in FIG. 7.
Figure 9B:
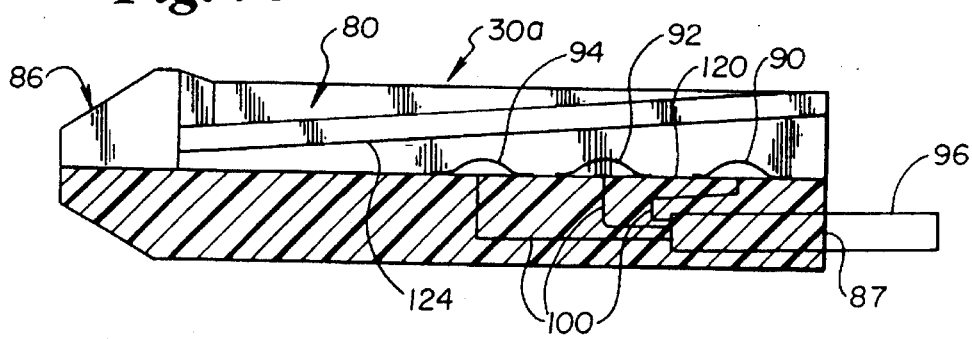
Figure 10A:
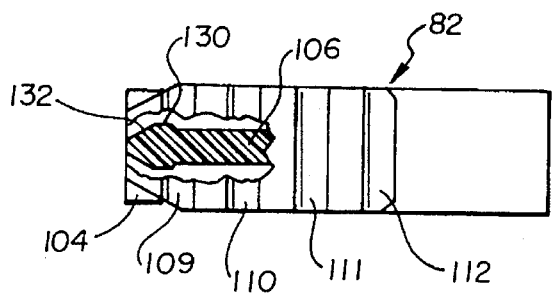
FIG. 10a illustrates a top plan view of the sliding member portion of the coupling mechanism shown in FIG. 7. Part of the sliding member's distal end is broken away and shown in section.
Figure 10C:
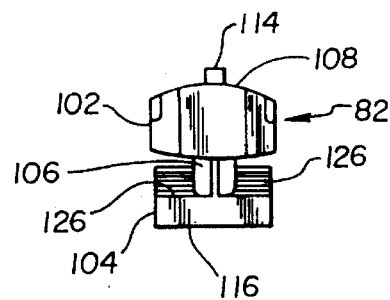
Figure 10B:
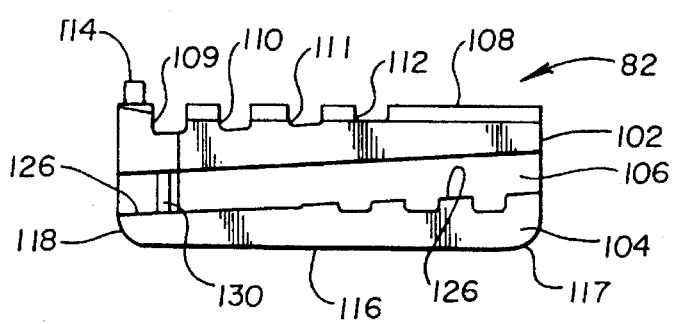

The operative, opposed surfaces of coupling mechanism 30*a* include bottom surface 120 of slot 80 on body member 78 (as shown in FIG. 9*b*) and bottom surface 116 on sliding member 82 (as shown in FIG. 10*b*). When the coupling mechanism 30*a* is assembled for use, these two opposed engagement surfaces are urged together to "trap" guide wire 22 therebetween, thereby securing the coupling mechanism 30*a* to the guide wire 22 at its proximal end, and also securing contact between the conducting layers 46, 48, 49, and the contacts 90, 92, 94.

Engagement surfaces 120 and 116 are brought together about guide wire 22 by a slide lock arrangement comprised of ramped surface 124 on body member 78 (see FIG. 9*b*) and ramped surface 126 on lower cross member 104 of sliding member 82 (see FIG. 10*b*). Ramped surface 124 has portions on each side of slot 80 and ramped surface 126 has portions on each side of center beam 106 (see FIG. 10*c*). Longitudinal insertion of sliding member 82 into slot 80 of a body member 78 causes ramped surface 126 on sliding member 82 to engage ramped surface 124 on body member 78, and as sliding member 82 is continually urged toward the distal end of body member 78, these two ramped surfaces 124 and 126 continue to engage. As a result, sliding member 82 is urged laterally "downwardly" into slot 80 as sliding member 82 moves toward the distal end of body member 78. Consequently, engagement surfaces 120 and 116 are urged together. In a preferred embodiment each ramped surface is offset by approximately four degrees from its respective engagement surface.

To prevent sliding member 82 from inadvertently separating from body member 78, a narrowing or constriction 128 of slot 80 at the proximal end of the body member 78 (see FIG. 9*a*) is provided, along with an enlarged flange 130 on a tapered distal portion 132 of central beam 106 of sliding member 82 (see FIG. 10*a*). As shown in FIG. 9*a*, an outwardly flared portion 134 of slot 80 at its proximal end facilitates reception of tapered distal portion 132 of central beam 106 of sliding member 82. Additional force is required to move sliding member 82 through the constricted portion 128 of slot 80 on body member 78 because it is narrower than the width of flange 130. To accommodate this, body 78 spreads slightly apart at constricted portion 128 of slot 80 when sliding member 82 is passed through constricted portion 128. Once enlarged flange 130 is distally past slot constriction 128, however, flange 130 acts as a stop (engaged by constriction 128) to prevent sliding member 82 from being inadvertently moved out of slot 80 in a proximal direction.

In a preferred embodiment, body member 78 of coupling mechanism 30*a* is formed from molded polycarbonate, and sliding member 82 is formed from molded polyvinylchloride (PVC). The PVC sliding member 82 is thus softer than the polycarbonate body member 78, and upon being urged into engagement with guide wire 22, lower cross member 104 of sliding member 82 will deform slightly about guide wire 22 and between surfaces 124 and 120 of body member 78. This deformation aids the coupling mechanism 30*a* in making an affirmative no-slip grip on guide wire 22. Of course, in another embodiment, body member 78 can be formed from a softer material than sliding member 82 and the gripping effect on guide wire 22 will be essentially the same. It is preferred (although not necessarily essential) that one of the opposed components be capable of some deformation upon moving sliding member 82 into engagement with guide wire 22 in order to achieve the desired "lock-down" effect of coupling mechanism 30*a* on guide wire 22.

Figure 11:
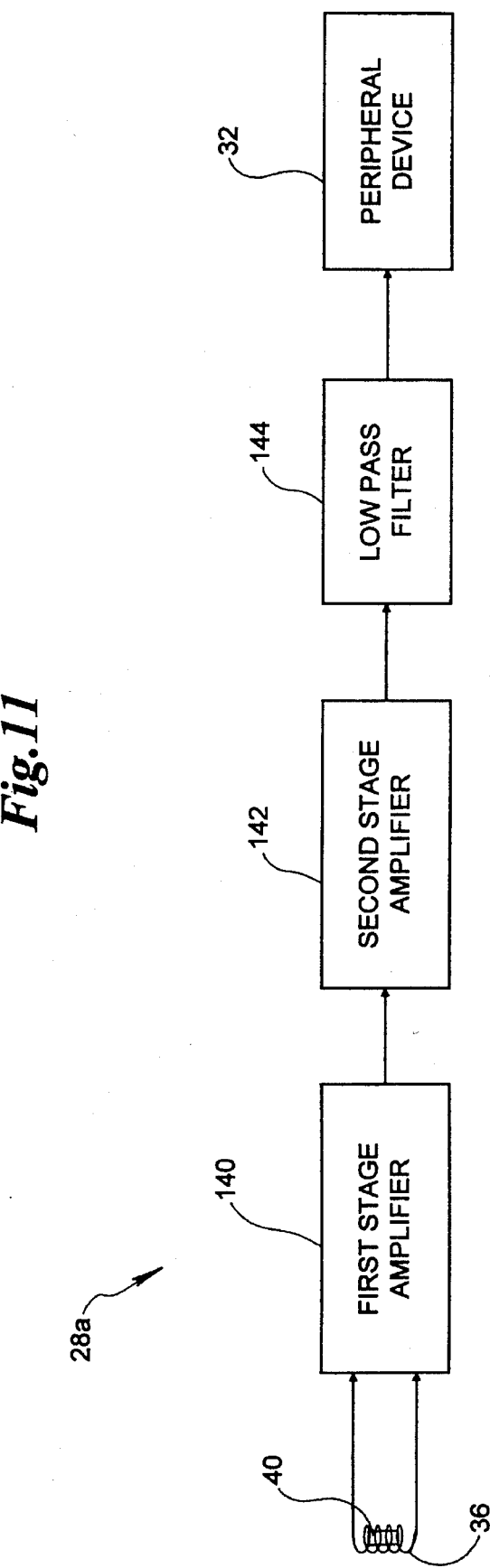
FIG. 11 is a block diagram illustrating a general embodiment of the processing circuitry shown in FIG. 1.

FIG. 11 illustrates at 28*a* a general block diagram of an acceptable configuration for the processing circuitry 28 shown in FIG. 1. The processing circuitry 28*a* may be of the general type used to process analog signals and convert them to sound or a visual representation. An example of such is the circuitry used to convert the mechanical vibrations imparted to a phonograph needle into sound outputs from a loudspeaker, or into a visual display on the phonograph's power amplifier. Such circuits are well known in the art and are generally referred to as phonographic pickup circuits. Additional examples are disclosed in U.S. Pat. Nos. 3,930,494 to Maurer et al.; 4,986,276 to Wright; and Volume 10 of Precision Monolithics' 1990 Data Book at 7–136. The entire disclosure of each of the above-identified documents is incorporated herein by reference. It is also contemplated that the processing circuitry 28 could be implemented using digital circuit components or a combination of digital and analog. The specific details of any one particular circuit, however, are not considered essential to this invention. Thus, the detailed circuit illustrated in FIG. 12 is provided only as an example.

The processing circuitry 28a shown in FIG. 11 includes a first stage amplifier 140 which accepts the output from the guide wire 22 and provides a gain of approximately 10,000. A second stage amplifier 142 adds a gain of 50 to 100, and a low pass filter 144 removes unwanted noise from the guide wire signal which is then passed to the peripheral device 32.

Figure 12:
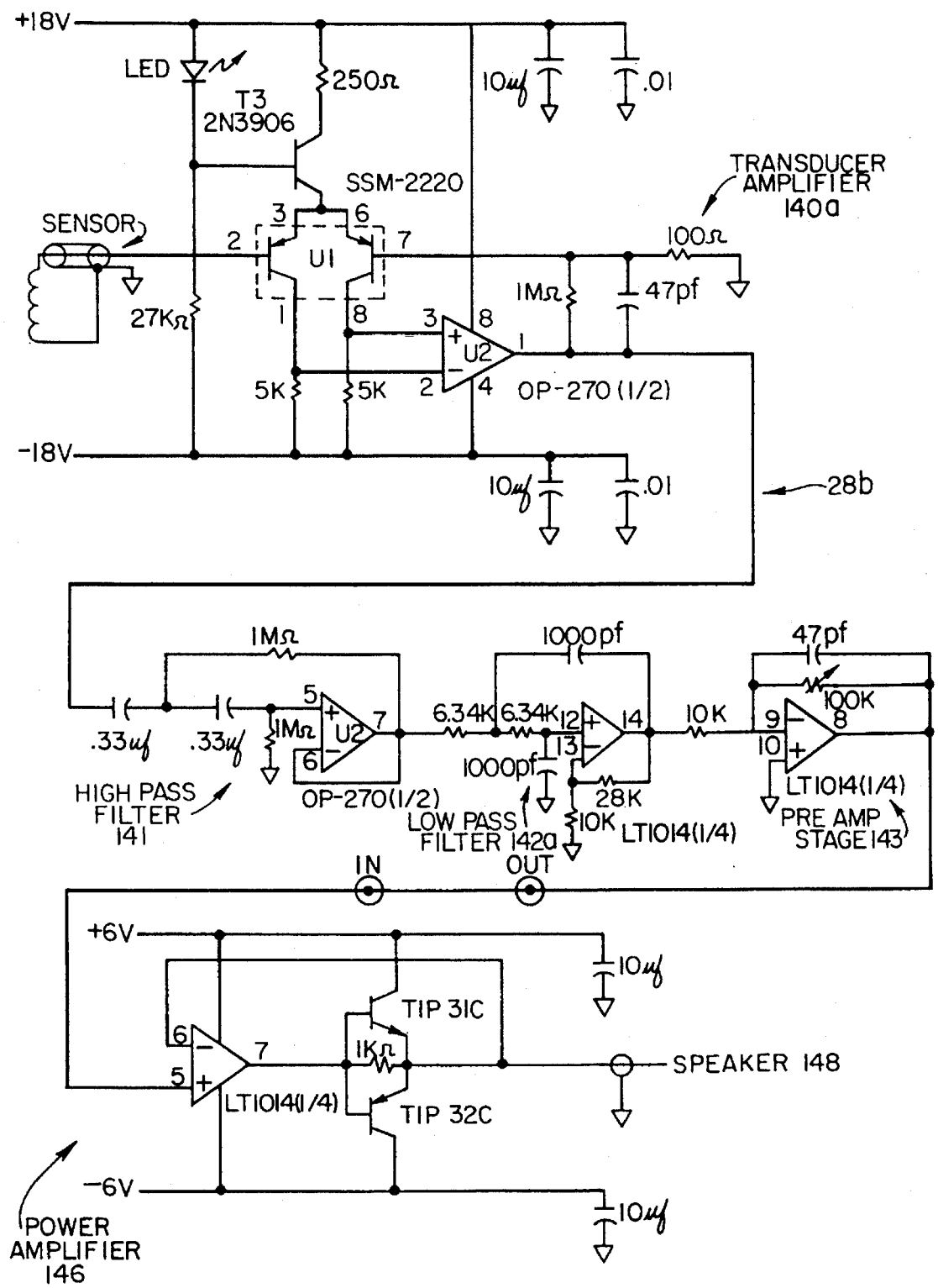
FIG. 12 is a schematic diagram illustrating a more detailed embodiment of the processing circuitry shown in FIG. 1.

FIG. 12 illustrates a specific processing circuit for converting the guide wire signals into audible sounds. The circuit 28b shown in FIG. 12 is known, and its particulars are not part of the disclosed invention. Accordingly, its specific elements will not be discussed in detail here. In general, the circuit 28b includes an amplifier 140a coupled to a high pass filter 141 which is coupled to a low pass filter 142a. The output of the low pass filter 142a is then coupled to a pre-amp stage 143 and then to a power amplifier 146 which is coupled to a loudspeaker 148. This circuit is sufficient to detect guide wire signals having a frequency up to approximately 70 Khz.

The embodiments described herein relate to a separate guide wire used with "over-the wire" catheters. However, the invention is equally applicable to a wide range of percutaneous transluminal devices, including "fixed-wire" catheters in which the guide wire is permanently attached at the distal end of the catheter. Additionally, the specific applications described herein for the vibration sensing-system 20 are not intended to be exhaustive. It is contemplated that the system 20 would be useful in any in vivo procedure in which vibrations are imparted to a transluminal device through some form of physical contact.

While the above-described embodiments of the invention are preferred, those skilled in this art will recognize modifications of structure, arrangement, composition and the like which do not part from the true scope of the invention. The invention is defined by the appended claims, and all devices and/or methods that fall within the meaning of the claims, either literally or by equivalents, are intended to be embraced therein.

We claim:

1. A percutaneous transluminal device comprising:

an elongate shaft having a distal end portion; and a spring tip transducer coupled to said distal end portion of said shaft, said spring tip transducer comprising a system which converts mechanical vibrations less than or equal to 70 kilohertz to electrical signals wherein said spring tip transducer senses said mechanical vibrations.

2. The invention defined in claim 1 wherein said spring tip comprises:

a piezoelectric crystal; and a sensing element coupled to said crystal.

3. A percutaneous transluminal device comprising:

an elongate shaft having a distal end portion; and a transducer coupled to said distal end portion of said shaft;

said transducer comprising:

a magnetic material; and an electrically-conductive coil within a magnetic field of said magnetic material and coupled to the shaft such that said coil experiences mechanical vibration when the transluminal device experiences mechanical vibration.

4. The invention defined in claim 3 wherein:

said elongate shaft comprises a guide wire having a spring tip; and said spring tip is said coil.

5. The invention defined in claim 3 further comprising:

processing circuitry coupled to said transducer; and a display coupled to said circuitry.

6. The invention defined in claim 3 further comprising:

processing circuitry coupled to said transducer; and an audio device coupled to said transducer.

7. The invention defined in claim 6 wherein said audio device is a loudspeaker.

8. The invention defined in claim 6 wherein the device further comprises:

at least one layer of conducting material extending along said shaft and coupled between said transducer and said processing circuitry.

9. A vibration sensing system comprising:

a percutaneous transluminal device having an elongate shaft and a distal end portion;

a spring tip transducer coupled to said transluminal device;

said spring tip transducer comprising a system which converts mechanical vibrations less than or equal to 70 kilohertz to electrical signals, wherein said spring tip transducer senses said mechanical vibrations;

processing circuitry coupled to said transducer; and a peripheral device coupled to said processing circuitry.

10. The system defined in claim 9 wherein said peripheral device comprises a loudspeaker.

11. The system defined in claim 9 wherein:

said transluminal device is a guide wire.

12. A method of performing a medical procedure in a patient's vascular system containing objects therein, the steps comprising:

inserting an elongate shaft into said patient's vascular system, said shaft having a spring tip transducer coupled to a distal end portion;

advancing said elongate shaft into said patient's vascular system such that said spring tip transducer contacts said patient's vascular system or objects therein; and sensing impacts imparted to said spring tip transducer.

13. The method defined in claim 12 further comprising the step of converting said impacts into an audible signal.

14. A method wherein impacts within a patient's system are sensed by:

providing a magnetic material for creating a magnetic field; and providing a sensing coil within said magnetic field and coupled to said shaft such that said sensing coil experiences mechanical vibration when the shaft experiences mechanical vibration;

wherein, movement of said sensing coil within said magnetic field generates electronic signals representative of the impacts imparted to said shaft.

15. A percutaneous transluminal device for use in connection with performing vascular therapy on a patient, the device comprising:

a guide wire having a spring tip and a distal end portion for insertion into a body vessel;

a transducer coupled to said distal end portion of said guide wire;

said transducer comprising a magnetic material creating a magnetic field; and said spring tip being within said magnetic field and experiencing mechanical vibration when said guide wire experiences mechanical vibration.

16. A percutaneous transluminal device for use in connection with performing vascular therapy on the inner surface of a patient's vascular system or objects within the patient's vascular system, the device comprising:

an elongate shaft having a distal end portion; and a transducer coupled to said distal end portion of said shaft, said transducer being exposed such that said transducer is adapted to contact said inner surface or objects in said vessel as said shaft is advanced through said vessel and converts impacts from 0–70 kilohertz imparted to said transducer into electronic signals.

17. A percutaneous transluminal device comprising:

an elongate shaft having a distal end portion; and a transducer coupled to said distal end portion of said shaft, said transducer comprising:

a magnetic material coupled to the shaft such that said material experiences mechanical vibration when the transluminal device experiences mechanical vibration; and an electrically conductive coil within a magnetic field of said magnetic material.

18. The invention defined in claim 17 further comprising:

processing circuitry coupled to said transducer; and a display coupled to said circuitry.

19. The invention defined in claim 18 wherein the device further comprises:

at least one layer of conducting material extending along said shaft and coupled between said transducer and said processing circuitry.

* * * * *